US00PP36622P2

(12) United States Plant Patent
van Swieten

(10) Patent No.: US PP36,622 P2
(45) Date of Patent: Apr. 22, 2025

(54) ***PHALAENOPSIS* PLANT NAMED 'PHA515727'**

(50) Latin Name: *Phalaenopsis hybrida*
Varietal Denomination: PHA515727

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/537,748

(22) Filed: Dec. 12, 2023

(51) Int. Cl.
*A01H 5/02* (2018.01)
*A01H 6/62* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./311
CPC ..... A01H 5/02; A01H 5/00; A01H 6/62
See application file for complete search history.

(56) References Cited

PUBLICATIONS

UPOV Pluto 20240908 for *Phalaenopsis* Pha515727 retrieved on Sep. 9, 2024 at https://pluto.upov.int/result, one page. (Year: 2024).*

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'PHA515727', characterized by its upright plant habit; moderately vigorous growth habit; strong flowering stems; strong leaves; freely flowering habit with typically two inflorescences developing per plant, each inflorescence with numerous flowers; white and reddish purple bi-colored flowers with yellow-colored labella; and good postproduction longevity.

2 Drawing Sheets

Figure 1:
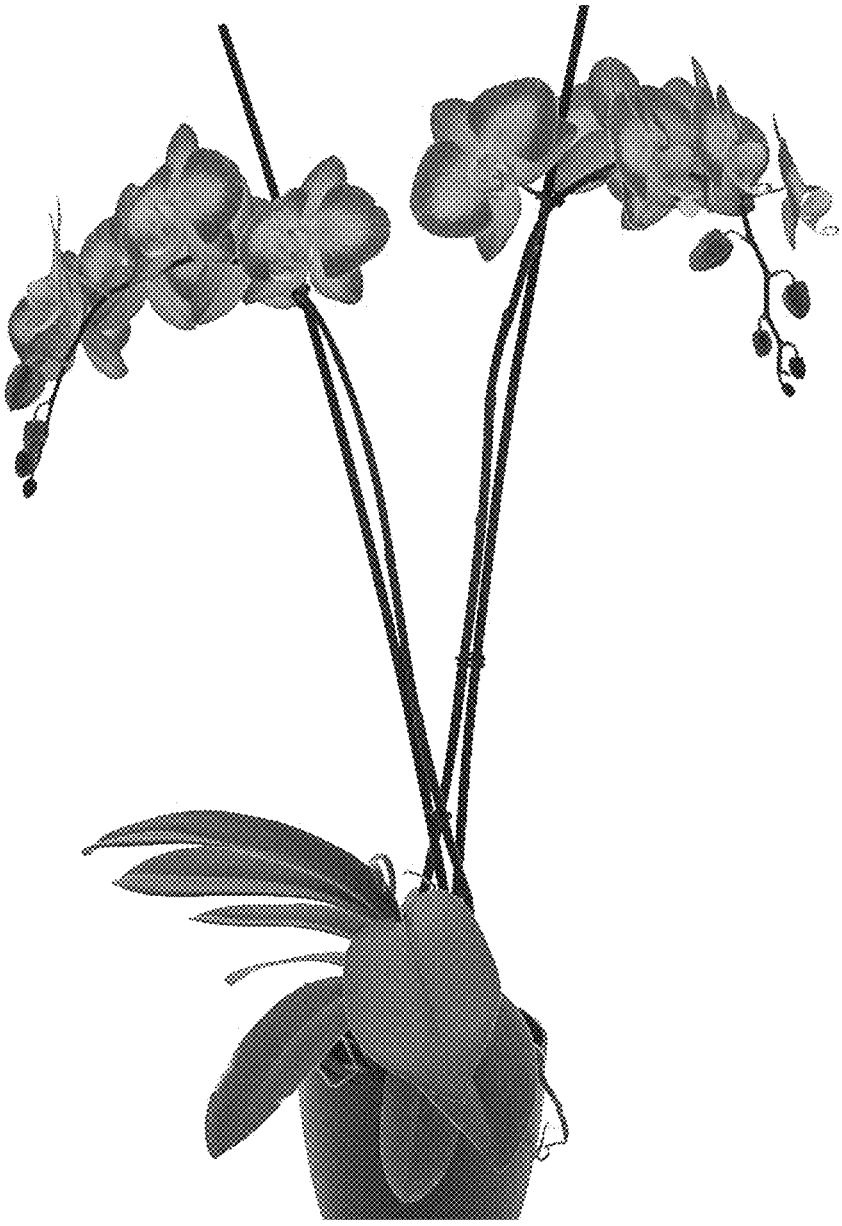

Botanical designation: *Phalaenopsis hybrida.*
Cultivar denomination: 'PHA515727'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B. V. of Bleiswijk, The Netherlands on Apr. 20, 2022, application number 2022/1062. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'PHA515727'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique and attractive patterns and coloration.

The new *Phalaenopsis* plant originated from a cross-pollination in January 2016 in Bleiswijk, The Netherlands of a proprietary selection of *Phalaenopsis hybrida* identified as code number 12-52030-02, not patented, as the female, or seed, parent with a proprietary selection of *Phalaenopsis hybrida* identified as code number 00001-4845, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in September 2018.

Asexual reproduction of the new *Phalaenopsis* plant by in vitro meristem propagation in a controlled environment in Bleiswijk, The Netherlands since September 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA515727'. These characteristics in combination distinguish 'PHA515727' as a new and distinct *Phalaenopsis* plant:

1. Upright plant habit.
2. Moderately vigorous growth habit.
3. Strong flowering stems.
4. Sturdy and healthy leaves.
5. Freely flowering habit with typically two inflorescences developing per plant, each inflorescence with numerous flowers.
6. White and reddish purple bi-colored flowers with yellow-colored labella.
7. Good postproduction longevity.

Plants of the new *Phalaenopsis* can be compared to plants of the female parent selection. Plants of the new *Phalaenopsis* differ primarily from plants of the female parent selection in the following characteristics:

1. Flower petal margins of plants of the new *Phalaenopsis* are very slightly or not imbricate whereas flower petal margins of plants of the female parent selection are very undulate.
2. Flower petals and sepals of plants of the new *Phalaenopsis* are white and reddish purple in color whereas flower petals and sepals of plants of the female parent selection are white and dark red in color.

Plants of the new *Phalaenopsis* can be compared to plants of the male parent selection. Plants of the new *Phalaenopsis* differ primarily from plants of the male parent selection in flower color as flower petals and sepals of plants of the new *Phalaenopsis* are white and reddish purple in color whereas flower petals and sepals of plants of the male parent selection are solid purplish red in color.

Plants of the new *Phalaenopsis* can be compared to plants of *Phalaenopsis hybrida* 'Phalipue', disclosed in U.S. Plant Pat. No. 33,312. In side-by-side comparisons, plants of the new *Phalaenopsis* differ primarily from plants of 'Phalipue' in the following characteristics:

1. Leaves of plants of the new *Phalaenopsis* are positioned outwardly to downwardly arching whereas leaves of plants of 'Phalipue' are positioned mostly outwardly.
2. Plants of the new *Phalaenopsis* have broader labella central lobes than plants of 'Phalipue'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA515727' grown in a container.

Figure 2:
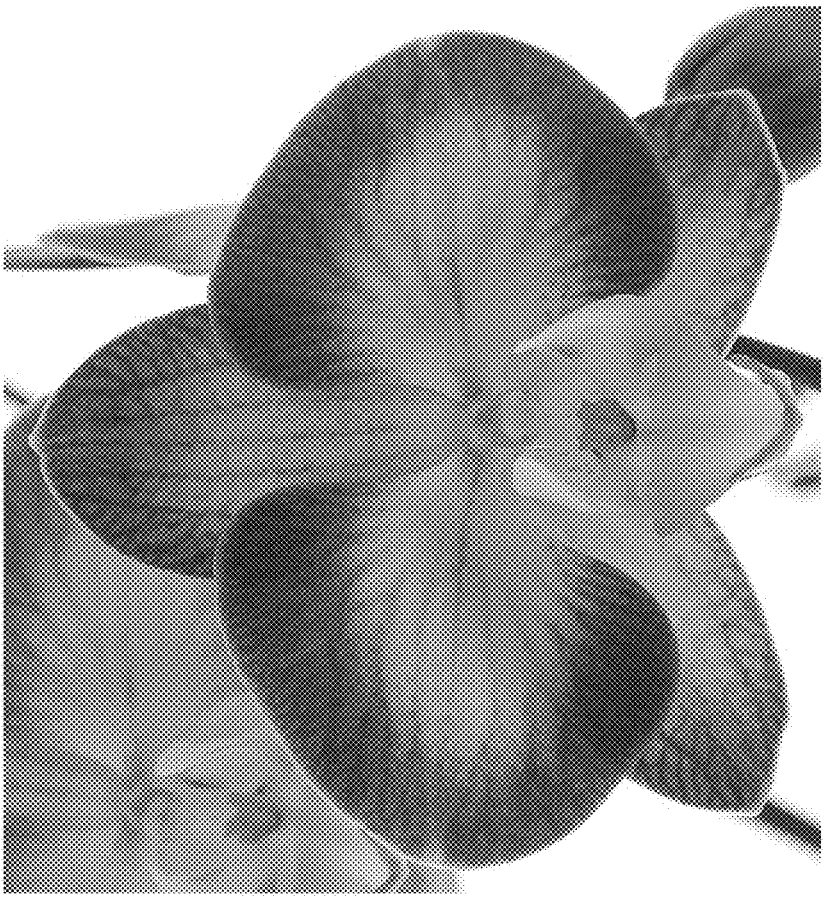

The photograph on the second sheet (FIG. 2) is a close-up view of a typical flower of 'PHA515727'.

DETAILED BOTANICAL DESCRIPTION

The aforementioned photographs and following observations and measurements describe plants grown during the summer in 12-cm containers in a glass-covered greenhouse in Bleiswijk, The Netherlands and under cultural practices typically used in commercial *Phalaenopsis* production. Plants were 18 months old when the photographs and description were taken. During the first 14 months of production of the plants, day and night temperatures averaged 28.5 C. During the final four months of production of the plants, day and night temperatures averaged 20 C. In the following description, color references are made to The Royal Horticultural Society Colour Chart, 2015 Edition, except where general terms of ordinary dictionary significance are used.

Botanical classification: *Phalaenopsis hybrida* 'PHA515727'.

Parentage:

*Female, or seed, parent*.—Proprietary selection of *Phalaenopsis hybrida* identified as code number 12-52030-02, not patented.

*Male, or pollen, parent*.—Proprietary selection of *Phalaenopsis hybrida* identified as code number 0001-4845, not patented.

Propagation:

*Type*.—By in vitro meristem propagation.

*Time to initiate roots, summer and winter*.—About two weeks at temperatures about 28 C to 30 C.

*Time to produce a rooted young plant, summer and winter*.—About 20 to 25 weeks at temperatures about 28 C to 30 C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane*.—About 9.9 cm.

*Plant height, substrate level to top of floral plane*.—About 50 cm.

*Plant diameter or spread*.—About 36.6 cm.

Leaf description:

*Arrangement and quantity*.—Distichous, simple; sessile; about four fully-developed leaves per plant.

*Length*.—About 19 cm.

*Width*.—About 6 cm.

*Aspect*.—Outwardly to downwardly arching.

*Shape*.—Narrowly oblong to oblanceolate; slightly carinate.

*Apex*.—Unequal acute.

*Base*.—Sheathing. Sheath length: About 2.5 cm. Sheath width: About 1.3 cm. Sheath color: Close to 144A; margins, tinged with close to 177A and 177B.

*Margin*.—Entire; not undulate.

*Texture and luster, upper surface*.—Smooth, glabrous; slightly glossy.

*Texture and luster, lower surface*.—Smooth, glabrous; moderately glossy.

*Venation pattern*.—Camptodromous.

*Color*.—Developing leaves, upper surface: Close to 137A and 137B; fine dots, close to 138A and 138B. Developing leaves, lower surface: Close to 146A; fine dots, close to 146B; towards the margins, close to 148A. Fully expanded leaves, upper surface: Close to a blend of 137C and 146A; venation, close to 137A to 137B. Fully expanded leaves, lower surface: Close to 146B; towards the margins, tinged with close to a blend of 147A and 147B; venation, close to 143A.

Inflorescence description:

*Appearance and flowering habit*.—Showy zygomorphic flowers arranged on axillary simple racemes; typically two inflorescences develop per plant; each inflorescence with about twelve flowers; flowers face outwardly on outwardly arching inflorescences supported by upright peduncles; flowers with three petals, two lateral petals and one center petal transformed into a labellum and three sepals; viewed from a lateral perspective, flowers mostly flat.

*Fragrance*.—None detected.

*Time to flower*.—Plants begin flowering about five months after planting; plants flower naturally during the winter into the spring.

*Flower longevity*.—Long flowering period, inflorescences maintain good substance for about eleven weeks on the plant; flowers not persistent.

*Inflorescence length* (*lowermost flower to inflorescence apex*).—About 28.4 cm.

*Inflorescence width*.—About 13.1 cm.

*Flower buds*.—Height: About 1.6 cm. Diameter: About 1 cm by 1.3 cm. Shape: Broadly ovate. Color: Close to 161A; distally, strongly tinged with close to 187C.

*Flower size*.—About 8.2 cm (vertical) by 9.3 cm (horizontal).

*Flower depth*.—About 3.1 cm.

*Petals, quantity and arrangement*.—Three, two lateral petals and one center petal transformed into a labellum.

*Lateral petals*.—Appearance: Viewed from a lateral perspective, lateral petals mostly flat and free, that is, not imbricate. Length: About 4.5 cm. Width: About 5.3 cm. Shape: Close to lunate to broadly reniform. Apex: Obtuse to shallowly retuse. Margin: Entire; not undulate. Texture and luster, upper and lower surfaces: Smooth, glabrous, velvety; matte. Color: When opening, upper surface: Close to N78B; narrow margin edges, close to 76C; at the base, close to NN155D; venation, close to N78A. When opening, lower surface: Close to a blend of 77B and 77C; centers and narrow margin edges, close to 76C; at the base, close to NN155C; venation, close to 77A to 77B. Fully opened, upper surface: Close to N78B and N78C; proximal central blotch, close to N78D; narrow margin edges, close to 76C; at the base, close to NN155D; venation, close to N78A and N78B; color does not change with subsequent development. Fully opened, lower surface: Close to N78C; centers, close to a blend of 76C and N155A; narrow margin edges, close to 76C; at the base, close to NN155D; venation, close to N78B; color does not change with subsequent development.

*Labella*.—Appearance: Three-parted with two lateral lobes and a central lobe. Length, lateral lobes: About 2 cm. Width, lateral lobes: About 1.5 cm. Length, central lobe: About 2.3 cm. Width, central lobe: About 7 mm to 25 mm. Length, cirrhose tips: About 1.5 cm. Shape, lateral lobes: Obovate. Shape, central lobe: Deltoid. Apex, lateral lobes: Obtuse. Apex, central lobe: Cleft with two upwardly reflexed cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 4 mm in length, about 5 mm in width and about 5 mm in height. Color: When opening, upper surface: Lateral lobes: Close to NN155D; towards the base, close to 157D; small distal blotch, close to 63A; proximal margins, close to 7B. Central lobe: Close to 3A; towards the apex, close to NN155C with apical edge, close to NN74C; at the base, close to NN155D; cirrhose tips, close to 164B and 164C tinged with close to 182A and apices, close to 4D. Callosities: Close to 3A and tinged towards the base with close to 165A. When opening, lower surface: Lateral lobes: Close to NN155D; towards the base, close to 157D; small faint distal blotch, close to 63B; proximal margins, close to 7C. Central lobe: Close to 3A; towards the apex, close to NN155C with apical edge, close to NN74C tinged with close to 164B and 164C; at the base, close to 155A; cirrhose tips, close to 164B and 164C tinged with close to 182A and apices, close to 4D. Fully opened, upper surface: Lateral lobes: Close to NN155D; towards the base, close to 13A to 13D; small distal blotch, close to 63B; proximal margins, close to 13B. Central lobe: Close to 12A; towards the apex, close to NN155D with apical edge, close to NN74C; at the base, close to NN155D; cirrhose tips, close to 164B and 164C tinged with close to 182A and apices, close to 13A. Callosities: Close to 13A and 13B and tinged towards the base with close to 164A. Fully opened, lower surface: Lateral lobes: Close to NN155D; towards the base, close to NN155A; small faint distal blotch, close to 63B; proximal margins, close to 13A. Central lobe: Close to 11A; towards the apex, close to NN155D with apical edge, close to NN74C tinged with close to 164B and 164C; towards the margins, close to 13A; at the base, close to 155C; cirrhose tips, close to 164B and 164C tinged with close to 182A and apices, close to 13A.

*Sepals*.—Quantity and arrangement: Three, one upper dorsal sepal and two lower lateral sepals. Length, dorsal sepal: About 4.6 cm. Width, dorsal sepal: About 3 cm. Length, lateral sepals: About 4.6 cm. Width, lateral sepals: About 2.8 cm. Shape, dorsal sepal: Broadly elliptic. Shape, lateral sepals: Ovate. Apex, dorsal sepal: Acute to minutely apiculate. Apex, lateral sepals: Acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to N78C and N78D; narrow marginal edges, close to 76C; at the base, close to NN155D; venation, close to N78A. When opening, lower surface: Close to 161D; towards the margins and apex, close to N78C and N78D; narrow marginal edges, close to 76C; venation, close to N78B and N77B. Fully opened, upper surface: Close to N78B; narrow marginal edges, close to 76C; towards the base, close to 76B and at the base, close to NN155D; venation, close to N78A; color does not change with subsequent development. Fully opened, lower surface: Close to N80C; towards the margins and apex, close to N80B; narrow marginal edges, close to 76C; venation, close to N80A; color does not change with subsequent development. Color, lateral sepals: When opening, upper surface: Close to 157D; towards the margins and apex, close to N78C; narrow margin edges, close to 76C; at the base, close to 150C; venation, close to N78A. When opening, lower surface: Close to 161D; towards the margins and apex, close to N77B and N78B; narrow margin edges, close to 76C; at the base, close to 145B; venation, close to 184B. Fully opened, upper surface: Close to NN155D; towards the margins and apex, close to N78D; narrow margin edges, close to 76C; at the base, close to 150D; venation, close to N78A and N78B; color does not change with subsequent development. Fully opened, lower surface: Close to N78C; towards the apex, close to N78B; towards the base, close to 76B and 76C and at the base, close to 150C; narrow margin edges, close to 76C; venation, close to N78A and N78B; color does not change with subsequent development.

*Peduncles*.—Length: About 61.3 cm. Diameter: About 5 mm. Strength: Strong. Aspect: Upright to outwardly arching. Texture and luster: Smooth, glabrous; matte. Color: Slightly darker than a blend of 147A and N189A; fine dots, close to 147C.

*Pedicels*.—Length: About 3.9 cm. Diameter: About 3 mm. Strength: Moderately strong. Aspect: About 80 degrees from peduncle axis. Texture and luster: Smooth, glabrous; matte. Color: Close to 75D; proximally, close to 148A and distally, close to 145D.

*Reproductive organs*.—Androecium: Column length: About 8 mm. Column width: About 5.5 mm. Column color: Close to 77B and 77C and distally, close to 76D. Pollinia quantity: Two. Pollinia diameter (per two pollinia): About 2 mm. Pollinia color: Close to 23A. Gynoecium: Stigma length: About 3 mm. Stigma width: About 4.5 mm. Stigma shape: Reniform. Stigma color: Close to N155A. Ovary length: About 7 mm. Ovary diameter: About 1 mm. Ovary color: Close to 150B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40 C and are suitable for USDA Hardiness Zones 10 to 12.

It is claimed:

1. A new and distinct *Phalaenopsis* plant named 'PHA515727' as herein illustrated and described.

* * * * *